(12) United States Patent
Spivak

(10) Patent No.: US 7,569,037 B1
(45) Date of Patent: Aug. 4, 2009

(54) ATOMIZING SPRAY APPARATUS AND METHOD

(76) Inventor: Paul Spivak, 761 Beta Dr., Mayfield Heights, OH (US) 44143

( * ) Notice: Subject to any disclaimer, the term of this patent is extended or adjusted under 35 U.S.C. 154(b) by 0 days.

(21) Appl. No.: 11/340,945

(22) Filed: Jan. 27, 2006

Related U.S. Application Data

(60) Provisional application No. 60/648,076, filed on Jan. 27, 2005.

(51) Int. Cl.
*A61M 35/00* (2006.01)
(52) U.S. Cl. .................. 604/289; 604/540; 604/368; 604/389; 604/249; 604/295; 604/296; 454/49; 454/50; 454/51; 454/52; 454/53; 454/54; 454/55; 454/56; 454/57; 454/58; 454/59; 454/60; 454/61; 454/62; 454/63; 454/64; 454/65; 454/66; 454/67; 454/187
(58) Field of Classification Search .............. 604/289, 604/540, 368, 389, 249, 295, 296; 454/49, 454/50, 51, 52, 53, 54, 55
See application file for complete search history.

(56) References Cited

U.S. PATENT DOCUMENTS 1,305,180 A * 5/1919 Throop ................. 118/313

| 6,387,081 | B1 * | 5/2002 | Cooper | 604/289 |
| 7,004,932 | B2 * | 2/2006 | Szurko | 604/289 |
| 2004/0073186 | A1 * | 4/2004 | Cameron | 604/389 |
| 2005/0193945 | A1 * | 9/2005 | Coffield et al. | 118/704 |
| 2006/0163382 | A1 * | 7/2006 | Spivak et al. | 239/200 |

* cited by examiner

*Primary Examiner*—Tatyana Zalukaeva
*Assistant Examiner*—Ilya Y Treyger
(74) *Attorney, Agent, or Firm*—John D. Gugliotta; Mandy Seuffert

(57) ABSTRACT

A method and apparatus for applying an atomized liquid solution upon a person, comprising a spray enclosure booth; an exhaust vent located below an anticipated user's facial area zone, the exhaust vent disposed within the bottom tray or a lower area of at least one wall or a lower area of a door and configured for exhausting ambient atomized liquid solution from the spray enclosure booth; a rigid conduit support defining a central air flow conduit connected to a bottom tray and pneumatically connected to an exhaust vent and providing structural integrity to the enclosure booth; an atomizing spray head assembly movably connected to the rigid conduit support and physically supported by the rigid conduit support; and an exhaust system configured to exhaust ambient atomized liquid solution from the spray enclosure booth by drawing atomized solution into the exhaust vent then through and out of the rigid conduit.

5 Claims, 10 Drawing Sheets

ATOMIZING SPRAY APPARATUS AND METHOD

CROSS REFERENCE TO RELATED APPLICATION

Figure 1:
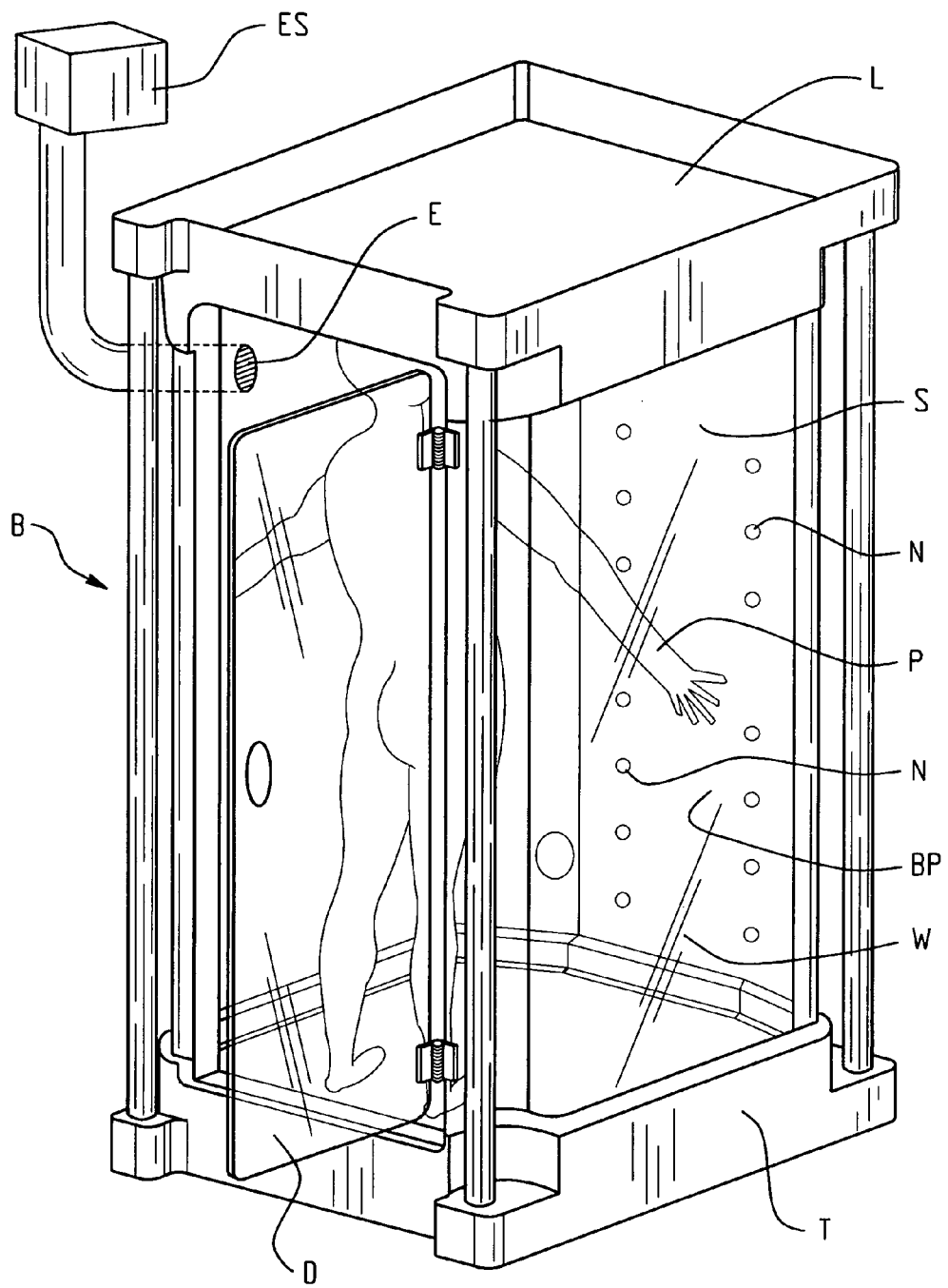
Figure 2A:
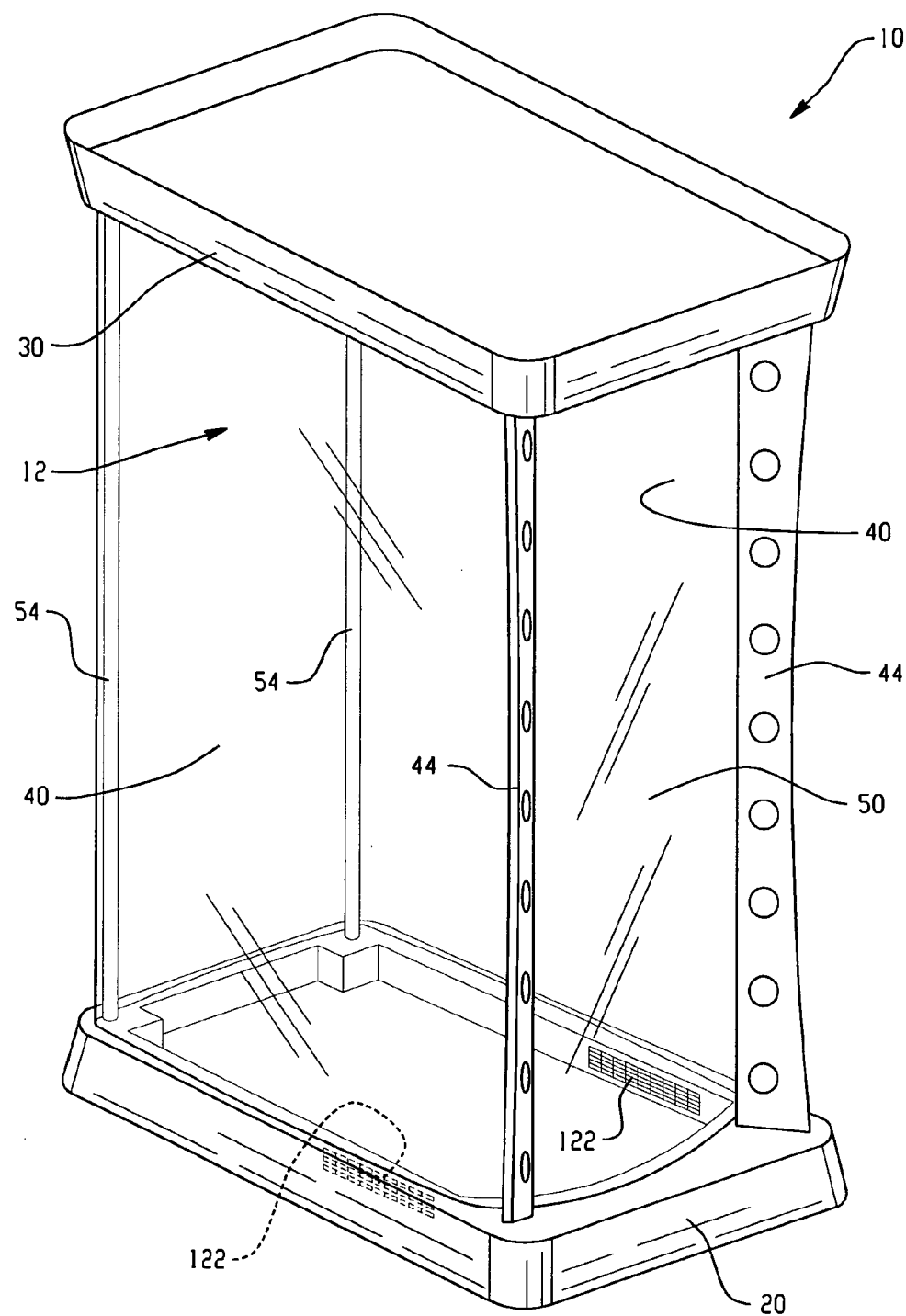
Figure 2B:
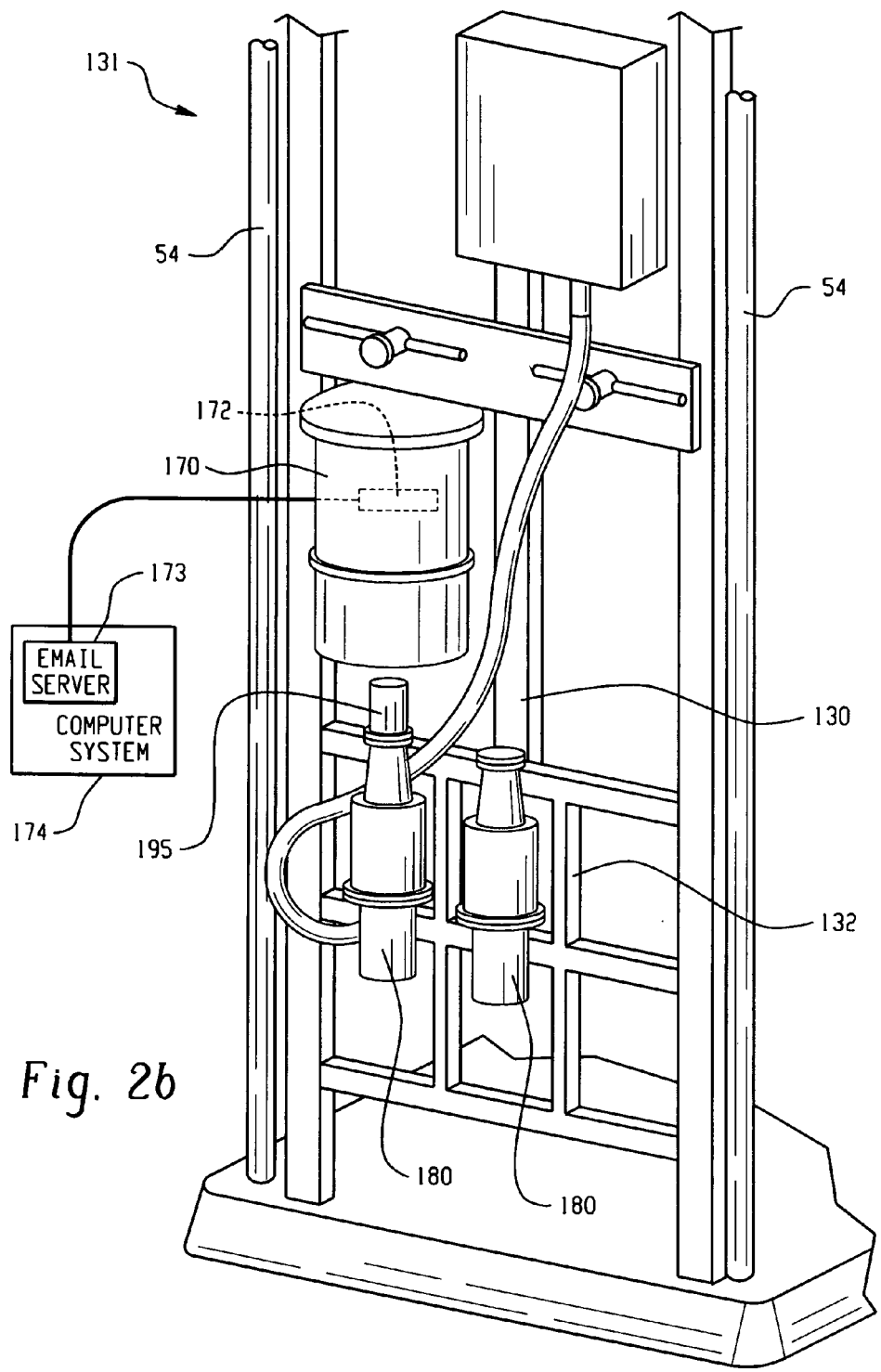
Figure 3:
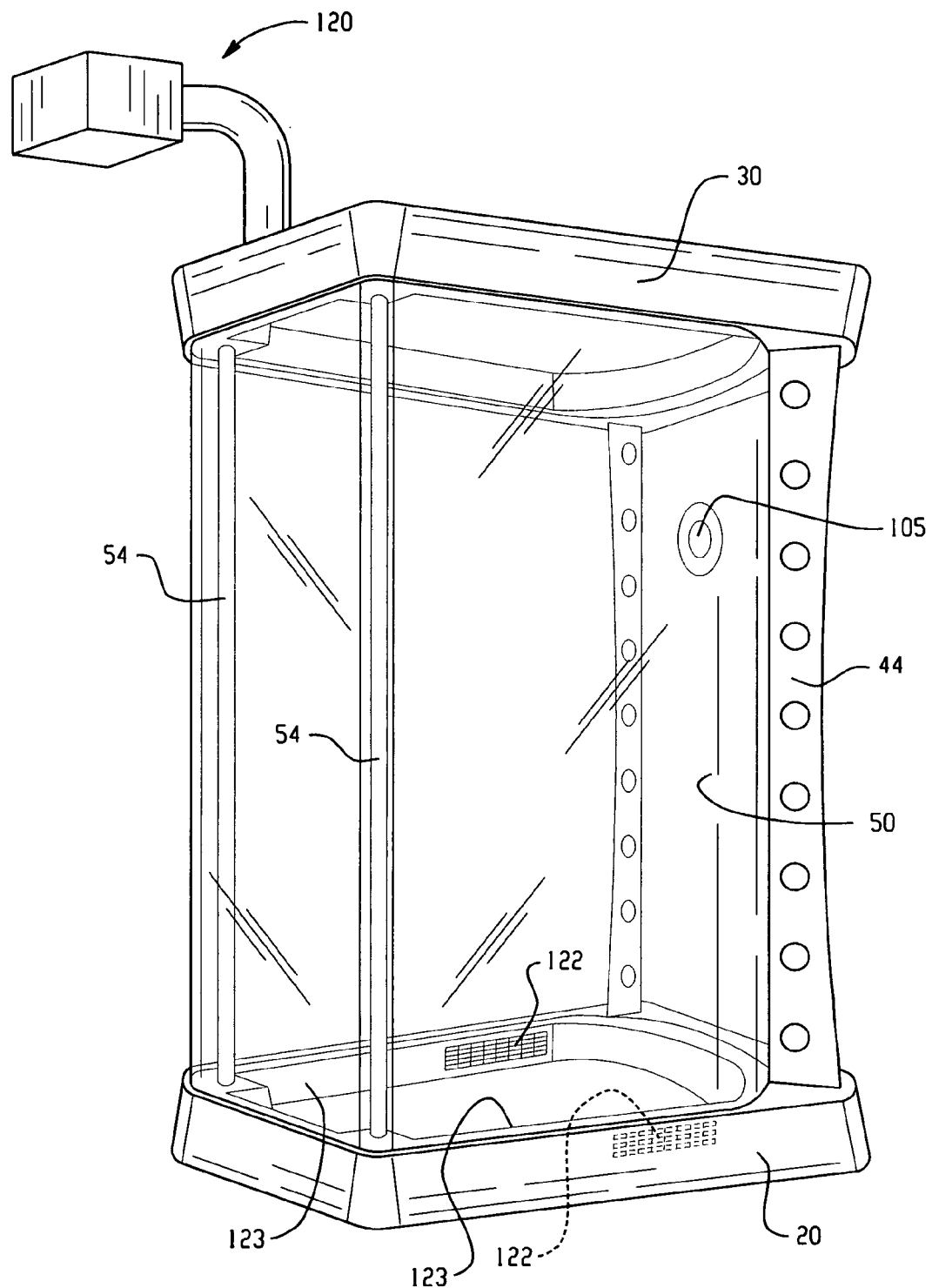
Figure 4:
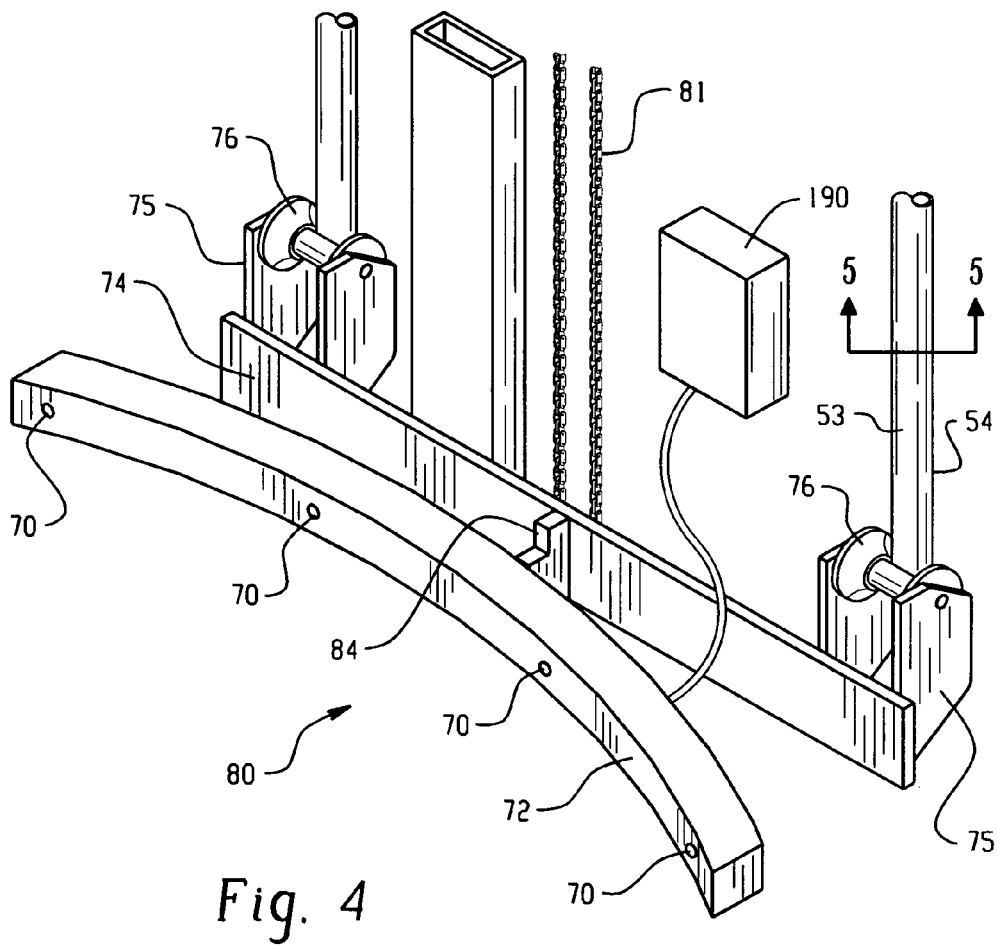
Figure 5:
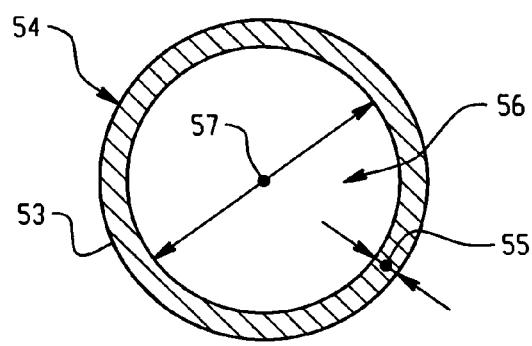
Figure 6:
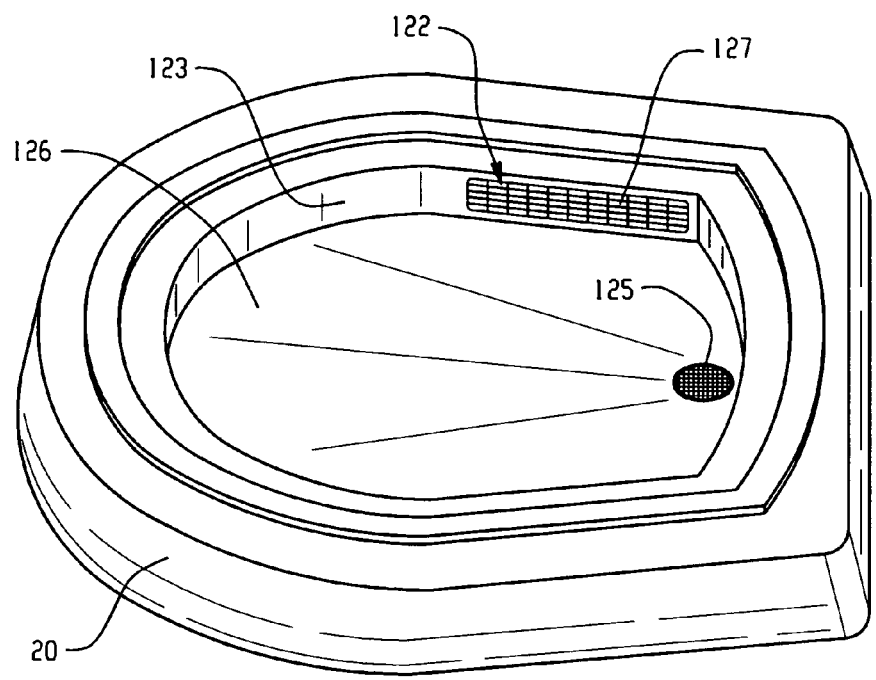
Figure 7:
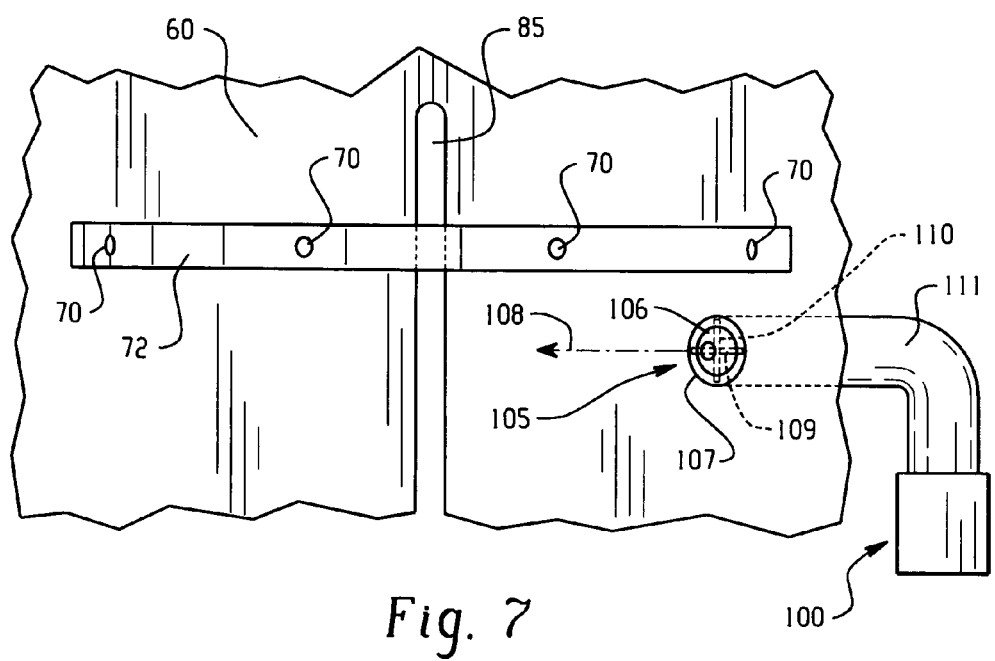

This application claims priority of provisional patent application Ser. No. 60/648,076, filed Jan. 27, 2005.

BACKGROUND OF THE INVENTION

Human skin tanning naturally occurs through environmental exposure to sunlight when the skin produces additional pigment (coloring) to protect itself against burning from ultraviolet radiation (UVR). Ultraviolet radiation, sometimes also called ultraviolet light, is invisible electromagnetic radiation of the same nature as visible light, but having shorter wavelengths and higher energies.

However, the reaction of any one person's skin to UVR present within sunlight is dependent upon the person's skin type and length and quality of exposure, and it is all too common for sunlight exposure to result in erythema, or "sunburn." In general, people with darker skin complexions can receive more UVR without erythema or suffering skin photo-aging or other upper skin layer damage. In contrast, people with extremely fair skin complexions may burn readily from even limited UVR exposure, and may not be able to effectively tan at all.

"Tanned" skin is generally considered physically attractive and a large market exists to serve people with "sunless" tanning systems. Sunless tanning systems provide a variety of means to achieve skin tanning without sunlight. Artificially-generated UVR lighting systems incorporated in tanning "beds" and "booths" are well-known, popular devices that utilize rows of fluorescent lighting tubes to project UVR upon a person in order to cause the person's skin to tan. Sunless tanning can also be achieved through the topical application of a variety of topical skin tanning solutions. Lotions and creams incorporating the color additive dihydroxyacetone (DHA) have been approved by the U.S. Food and Drug Administration for use in sunless tanning since 1977. DHA interacts with the dead surface cells in the outermost layer of the skin to darken skin color. Lotions containing DHA may be applied directly by hand, or through spray nozzle systems. Due to their convenience, spray nozzle systems that atomize the tanning lotion through an atomizing nozzle into a projecting mist have become very popular. They may be manually applied by an applicator moving the nozzle over the body of a person, or automatically applied through systems featuring moving or multiple nozzles, usually in combination with other apparatuses such as enclosures, booth structures, exhaust fans, re-circulating fans, and mist recovery systems.

However, the safe and efficient application of atomized sunless tanning mists upon a person presents a number of problems. In order to assure even application of the tanning products on a user to provide a subsequent evenly tanned appearance, the system must deliver a consistent and uniform quantity and quality of atomized mist upon the entire user, including the face and head areas, as well as the remainder of the body. This uniform application must be balanced with a desire to minimize the amount of atomized mist products inhaled by the user, or impinging upon the nasal, mouth and eye areas.

What are needed are improved sunless tanning systems and methods that provide means for minimizing inhalation and facial area soft tissue exposure of the atomized mist while assuring efficient and uniform application of the atomized mist on the skin areas of the user, in a cost and resource effective manner.

SUMMARY OF THE INVENTION

In one aspect a method and apparatus for applying an atomized liquid solution upon the skin of a person is provided, comprising a spray enclosure booth defined by at least one vertically oriented enclosure wall and a vertically oriented door, the at least one wall and the door disposed between and connected to a horizontally oriented bottom tray and a horizontally oriented top cap; an exhaust vent located below an anticipated user's facial area zone, the exhaust vent disposed within the bottom tray or a lower area of the at least one wall or a lower area of the door, the vent configured for exhausting ambient atomized liquid solution from the spray enclosure booth; a rigid conduit support having first and second ends and defining a central air flow conduit, the rigid conduit support first end connected to the bottom tray wherein the central airflow conduit is pneumatically connected to the exhaust vent, and the rigid conduit support second end is connected to and physically supporting the top cap and thereby providing structural integrity to the enclosure booth; an atomizing spray head assembly comprising at least one atomizing spray head, the spray had assembly movably connected to the rigid conduit support and physically supported by the rigid conduit support; and an exhaust system pneumatically connected to the rigid conduit support second end, whereby the exhaust system is configured to exhaust ambient atomized liquid solution from the spray enclosure booth by drawing said atomized solution into the exhaust vent then through and out of the rigid conduit support central air flow conduit.

In another aspect a downdraft exhaust method and apparatus is provided for removing an atomized liquid solution from an enclosure, comprising an enclosure booth defined by at least one vertically oriented enclosure wall and a vertically oriented door, the at least one wall and the door disposed between and connected to a horizontally oriented bottom tray and a horizontally oriented top cap; an exhaust vent located below an anticipated user's facial area zone, the exhaust vent disposed within the bottom tray or a lower area of the at least one wall or a lower area of the door, the vent configured for exhausting ambient atomized liquid solution from the spray enclosure booth; and an exhaust system pneumatically connected to the exhaust vent, whereby the exhaust system is configured to exhaust ambient atomized liquid solution from the enclosure booth by drawing said atomized solution into the exhaust vent downward relative to the anticipated user's facial area zone, and then out of the enclosure.

In another aspect the downdraft exhaust method and apparatus further comprises a positive pressure fresh air inlet vent configured to direct fresh air into the enclosure in the anticipated user's facial area zone.

In another aspect a method and apparatus for applying an atomized liquid solution upon the skin of a person is provided, comprising a spray enclosure booth defined by at least one vertically oriented enclosure wall and a vertically oriented door, the at least one wall and the door disposed between and connected to a horizontally oriented bottom tray and a horizontally oriented top cap; an atomizing spray head configured to apply an atomized liquid solution to a skin surface on a person; and a positive pressure fan dryer located in the enclosure top cap and configured to forcefully blow air down onto the skin surface of the person after the skin surface has received the atomized liquid solution from the atomizing spray head and dry the skin surface.

In another aspect a method and apparatus for continuously and automatically monitoring an amount of liquid solution in a reservoir is provided, comprising a solution reservoir containing an amount of liquid solution; and a sensor circuit located within the reservoir and in communication with a remote control system; wherein the sensor circuit is configured to measure the amount of liquid solution and send a notification signal to the control system responsive to the amount of liquid solution falling below a threshold amount.

In another aspect an atomizing spray head method and apparatus for applying an atomized liquid solution to a skin surface on a person is provided, comprising a spray nozzle assembly containing a solenoid element, the spray nozzle assembly further having a projection nozzle, wherein the solenoid is configured to vibrate responsive to the input pressure of a fluid entering the spray nozzle assembly, and wherein the solenoid vibration impacts the fluid entering the spray nozzle, the fluid impact causing the fluid to be projected from the projection nozzle in an atomized mist form.

In another aspect a method and apparatus for applying a temperature controlled atomized liquid solution upon the skin of a person is provided, comprising a liquid solution reservoir containing a liquid solution having a first temperature; a temperature modifying system connected to and receiving liquid from the reservoir, wherein the temperature modifying system is configured to change the first temperature into a second temperature; and an atomizing spray head in communication with and receiving liquid with the second temperature from the temperature modifying system.

In another aspect an atomizing spray head method and apparatus for applying an atomized liquid solution to a skin surface on a person is provided, comprising a liquid solution source configured to pump a liquid under pressure through a conduit; liquid solution pumped by the liquid solution source, the liquid solution having a liquid solution pressure; a spray nozzle connected to the conduit and configured to spray an atomized mist of the liquid solution with a projection pressure responsive to the liquid solution pressure; and the spray nozzle containing a pressure monitor element configured to measure the atomized mist projection pressure, the pressure monitor element in communication with the liquid solution source; wherein the liquid solution source is configured to change the liquid solution pressure responsive to an atomized mist projection pressure reported by the pressure monitor element.

BRIEF DESCRIPTION OF THE DRAWINGS

FIG. 1 is a side perspective view of a prior art spray tanning booth system. FIG. 2*a* is a front side perspective illustration of an atomizing spray booth 10 system according to the present invention.

FIG. 2*b* is a front side perspective illustration of the spray booth of FIG. 2. FIGS. 3 through 8 illustrate elements of the spray booth of FIG. 2 wherein some elements are depicted in relation to others for purposes of clarity, and these views are not complete exploded views of the spray booth of FIG. 2.

FIG. 9 is a front side perspective illustration of another atomizing spray booth system according to the present invention.

FIGS. 10 to and 11 illustrate elements of the spray booth of FIG. 9 wherein some elements are depicted in relation to others for purposes of clarity, and these views are not complete exploded views of the spray booth of FIG. 9.

FIG. 12 is a partial detailed view of FIG. 11 above.

DESCRIPTION OF THE INVENTION

The present invention relates generally to a method and apparatus comprising a plurality of atomizing spray nozzles configured to distribute an atomized liquid mixture within a designated area. More particularly, embodiments of the present invention are adapted to spray a tanning mixture upon a human person in a novel coordination with a novel ventilation and moving nozzle system.

Referring now to FIG. 1, a typical prior art atomizing spray booth B is illustrated. A user P typically enters into booth B, and closes the door D behind him. With the door D closed, the user P is now in a more or less sealed containment enclosure defined by the clear sidewalls W, the door D, and the bottom tray T in the upper lid element L. The user P then initiates a spray sequence, where red and one or more atomizing spray nozzles N compel an atomized mist of liquid tanning and/or bronzing solution toward and upon the user P. In some prior art booth systems, the atomizing nozzles N are fixed in a matrix array on the back panel BP. In other systems, one or more nozzles move up and down and/or side to side while atomizing the fluids and, in some systems, an air circulating system is incorporated to move the atomized mixture throughout the booth. In all of the systems, it is important to compel the atomized mixture onto a desired portion or on the entire user P to ensure application of the tanning and/or bronzing solutions.

Prior art spray tanning booth systems, such as the booth B illustrated in FIG. 1, also typically incorporate a ventilation and/or atomized mist removal system. Various approaches have been used to coordinate ventilation and mist removal functions with the application of the mist to minimize inhalation and soft tissue exposure.

FIG. 2 illustrates an atomizing spray booth system 10 and method according to the present invention. FIGS. 3 through 7 illustrate the elements of a spray booth 10 in a series of partially complete views, wherein some of the structural elements have been removed to provide for clarity in depicting and describing those elements present. The booth 10 provides an enclosure 12 defined by a bottom tray 20, a top cap element 30, sidewalls 40, a front door 50 and a rear wall 60, the enclosure 12 provided for receiving a user within an enclosed environment for the application of an atomized liquid solution through one or more atomizing spray nozzles 70.

In the present embodiment, the sidewalls 40, front door 50, and rear wall 60 are all formulated from polycarbonate acrylic materials, although it is readily apparent that glass or other rigid translucent materials may be used. By using translucent materials for the door 50 and sidewalls 40, light can be provided into the enclosure 12 from outside sources, either through general room lighting or through sunlight. Alternatively, mirrored or one-way opaque panels may be used wherein light will be admitted into the enclosure 4; however, a user will not be readily apparent to a viewer from outside the enclosure. Suitable materials for the top cap 30 and bottom tray 20 are hand-laid fiberglass composite materials, with a foot per unit measurement well known to those skilled in the art. Both cap 30 and tray 20 may also be formed from a common tray/cap element, providing efficiencies in design and manufacture.

The booth apparatus 10 is configured to apply any number of atomized liquid compositions. An illustrative but not exhaustive list of examples includes self-tanning formulations, sunscreens, suntan lotions, tanning accelerators, sunburn treatments, insect repellants, skin toners, skin bleaches, skin lighteners, anti-microbial compositions, moisturizers, exfoliants, nutriments or vitamins, massage aides, muscle relaxants, skin treatment agents, burn treatment agents, decontamination agents, cosmetics, wrinkle treatments or removers.

What is new in the present invention is a structure and method for efficiently and effectively applying atomized liquid compositions upon the user through coordination of a novel ventilation and nozzle application system that minimizes inhalation and facial area soft tissue exposures.

Multi-Function Vertical Support Structures

The spray booth 10 provides for two front structural support elements 44 and two rear structural support poles 54. The support elements 44 and support poles 54 are attached to the bottom tray 20 and are connected to and support the top cap 30. It is to be understood that in some embodiments of the invention the rear structural support poles 54 may, in fact, provide all of the vertical and lateral support needed to supportively connect the top cap, sidewalls, door, bottom tray and rear wall elements into a user booth enclosure structure. What is new is that the poles 54 provide three functions: (1) provide structural support for the booth itself; (2) function as support glides for a moving array assembly 80 of spray heads 70; and (3) define ventilation shafts for a novel downdraft ventilation system according to the present invention.

In the present embodiment, four atomizing spray nozzles 70 are provided in a curved nozzle rack 72. It will be readily apparent that more or less nozzles 70 may be provided, and the invention is not limited to the embodiment described herein. The rack 72 is attached to a support bar 74 by a central mounting bracket 84 and, at both ends of the bar 74, roller assemblies 75 are provided. A pair of convex rollers 76 within each roller assembly 75 is configured to roll upon the outer surface 53 of the support poles 54. Thus, the four atomizing spray nozzles 70 are aligned generally perpendicular to the support poles 54, and the entire assembly 80 is configured to smoothly convey up and down the support poles 54 responsive to a drive chain 81 driven by drive motor 82. The rear booth wall 60 defines a tall, narrow conveyance aperture 85, along which the central mounting bracket 84 travels. Thus, the spray nozzle arm 72 may travel up and down within the booth 10 enclosure area 12, while the remainder of the moving spray nozzle apparatus 80 remains behind the rear wall 60 and, therefore, outside of the user's booth enclosure area 12.

Prior art atomizing spray booth systems typically locate exhaust vents E in the upper regions of the booth B near the face of a user P, wherein the exhaust vents E were typically connected to external exhaust systems ES. This vent E location is conventional in that it is generally believed to more rapidly exhaust the ambient atomized mixture from the face regions when compared to regions distal from the user's face area, such as lower areas of the booth, thereby minimizing inhalation of the atomized mist.

Downdraft Ventilation System

What is also new is that the present invention provides for a downdraft ventilation system comprising an upper fresh air inlet system 100 and a bottom downdraft exhaustive vent system 120. Low-vent exhaust configurations have been avoided by prior art systems due to inefficiencies and cost factors. As prior art exhaust systems are typically located relatively high in the booth structure, additional hosing or exhaust conduit must be provided to incorporate low exhaust vents, presenting engineering and assembly difficulties and inefficiencies. By using hollow support poles 54 with cylindrical center voids 56 as conduit, the present invention can locate two exhaust vents 122 in the floor, one on each side wall of the bottom tray 20, pneumatically connected through channel voids formed in the bottom tray 20, which are also pneumatically connected to the pole voids 56 at the bottom of the support poles 54. The tops of the support poles 54 are pneumatically connected to a negative pressure exhaust fan system 120, which thereby exhaust air entrained atomized mist out of the booth through the floor vents 122. By connecting the support poles 54 directly to the exhaust fan system, no external conduit or other vent hose structures are required, which makes the entire exhaust system of the present invention much more efficient, and presents a cleaner look when compared with other prior art exhaust systems.

Therefore, what is important is that by providing hollow support poles 54 with a substantial interior diameter, the support poles can thereby serve an additional function as exhaust conduits through the centers of the poles 54. One embodiment of the three-function support/downdraft/roller guide pole 54 is fabricated from "100,000 stick," or about a tenth of an inch thick aluminum, and formed into a cylindrical tube having an outside diameter of about 3.5 inches, thus having an interior void diameter 57 of about 3.3 inches. However, other appropriate materials and thicknesses for fabrication will be readily apparent to one skilled in the art, and the present invention is not restricted to the embodiments described herein. It will be readily apparent that any number of interior void diameters 57 may be selected to provide exhaust conduit functions.

In the present embodiment, two side-mounted vents 122 are provided, one on each side wall 123 and generally opposing each other. A drain 125 is also provided, wherein the floor surface 126 pitches toward the drain 125 to enable the collection and draining of condensed atomized liquids as well as any solution from wash-down procedures. An advantage of the present embodiment is that locating the vents 122 on either side wall 123 provides for easier and more efficient and less costly direct connections to the venting support poles 54, without having to form a common chamber throughout the entire bottom tray 20 with the drain 125 or, alternatively, without requiring independent conduit routing below the entire common bottom tray floor surface 126, which may be the case where vents are provided on the bottom floor, such as the large combined drain and exhaust vent 225 illustrated in bottom tray 220 of another embodiment 200 of the present invention in FIGS. 8-10.

Another advantage of locating the side vents 122 laterally normal to and above the tray floor surface 126 is that the amount of wash-down or precipitating atomized fluid entering the vents 122 is minimized. By utilizing downwardly oriented louver vent grills 127, the downward orientation of the louvers 127 further prevents the entry of precipitating and downward flowing liquids into the vents 122; therefore, providing for superior cleanliness and lower sterilization requirements when compared to floor surface venting.

It will also be readily apparent that the exhaust vents taught by the present invention may alternatively be located in lower regions of enclosure walls or door(s). What is important is that the exhaust vent(s) are located below the anticipated facial area locations of users utilizing the booth. The lower that the exhaust vent is situated relative to the user's face, the greater the extent that the exhausting of the ambient atomized mixture will entail movement of the ambient mist downward and away from the facial areas.

Snorkel Inlet Ventilation

Another important advantage of present invention is the coordination of a snorkel inlet ventilation component 105 with the downdraft exhaust system 120. Prior art spray systems conventionally provide for exhaust vents near the anticipated face regions of the user and, therefore, in the upper areas of the booth. A disadvantage of this type of prior art setup is that, by providing an exhaust venting in the upper areas, the atomized mist is disturbed, which may result in ineffective application of the atomized mist to the face and upper areas. Another significant disadvantage is that these exhaust vents necessarily pull the ambient atomized mist directly around and across the face and, therefore, actually increase inhalation exposure during the operation of the exhaust system, typically prolonging the actual inhalation exposure time period. Atomized mist from all over the booth is thereby brought directly across the facial areas when prior art upper area exhaust systems are turned on throughout the entire exhausting period, increasing the amount of atomized mist being inhaled, bringing mist up from the bottom and right past the face. Therefore, the prior art upper area exhaust systems cannot be effectively operational during the spray sequence, and exposure to the lingering ambient atomized mist is created when it is drawn past the facial areas.

What is new in the present invention is the provision of an upper area snorkel fresh air inlet ventilation system 105. In the present embodiment, this inlet ventilation system 105 comprises a directional, generally cylindrical "snorkel" nozzle 106 in communication with a positive pressure fan unit 100, wherein the fan unit 100 blows fresh air into the booth 10 through the snorkel nozzle 106. The snorkel nozzle 106 may be manually or automatically adjusted to direct the incoming air flow directly into the facial area of the user. This may be accomplished by connecting the snorkel nozzle 106 to and within a cylindrical housing 107 with a common central axis 108 through a horizontal pivot pin 109 and a vertical pivot pin 110, wherein the snorkel nozzle 106 may pivot up-and-down on the horizontal pin 109 and may also pivot side-to-side on the vertical pin 110. As will be readily apparent to one skilled in the art, the snorkel nozzle 106 may also be configured to be automatically aimed and/or adjusted to direct the incoming air flow directly into the facial area of the user through a motorized mechanism coupled with a vicinity detection system.

Thus, with the present invention, atomized mist is exhausted by pulling the mist downward, away from the facial areas of the user when the exhaust system is initiating, said movement being further enhanced by the introduction of positive air pressure by the snorkel system 105 in the upper areas of the booth, and directed towards the facial areas. Therefore, atomized mist occurring in regions below the facial area are necessarily pulled away from the facial areas of the user by the downdraft exhaust system 120, said movement enhanced by "pushing" the mist downward as well by the introduction of positive pressures in the upper areas by the snorkel inlet system 105, thus providing significant improvements in the prevention and/or minimization of ambient mist inhalation exposure.

Although the snorkel system 105 of the present embodiment incorporates its own fan to generate positive pressure and positively put fresh air in front of the user's face, positively blowing fresh air at the facial areas and displacing the mist from nose and mouth, in some embodiments and applications the snorkel system may only passively direct air flow towards the face of a user. For passive air inlet applications, negative pressures within the booth relative to the outside atmosphere caused by the exhaust fan system may be enough to compel air flow through the snorkel system toward the user's face.

Another advantage of the present invention is the improved efficiency and use of system resources provided by the coordination of the application of atomized mist by the spray nozzles 70 with the snorkel inlet ventilation system 105 and the downdraft exhaust system 120. In the present embodiment, the spray bar 72 performs a complete spray atomizing sequence in a seven-second procedure. Beginning at the base of the booth 10, the spray nozzles 70 project atomized mixture toward the bottom of a user (and, therefore, at the user's feet) while the spray bar 72 rises toward the top of the booth 10 and past the user's facial areas in 3.5 seconds, and then continues to spray while the spray bar 72 moves back down toward the bottom of the booth in another 3.5 seconds. It has been found to provide satisfactory results in diminishing inhalation hazards and still assure a timely and efficient coating of the mist upon a user that the positive pressure snorkel inlet system 105 and the downdraft exhaust system 120 start operating immediately upon the beginning of the seven-second spray sequence.

When the spray bar 72 comes up to the face-area level of the user during the initial 3.5 second rising phase, the snorkel inlet system 105 temporarily shuts down so it will not disturb the sprayed mist, enabling application of the mist on the facial and head areas. The shutdown typically is configured to occur only while the spray bar is near the face area. Thus, the snorkel inlet system 105 remains shut down until the spray bar 72 has reached the top of its travel, and begun its descent downward to a point past the facial area, whereupon the snorkel inlet system 105 comes back on. One possible timing for this on-and-off cycling of the snorkel inlet system 105 for a seven-second total spray sequence is where the snorkel in the system 105 turns off at the two second mark of the 3.5 second rising period (thus, off for the last second and a half) and remains off for the first 1.5 seconds of the 3.5 second downward travel epoch of the spray bar 72, turning back down for the last two seconds of the total seven-second spray sequence. This results in the snorkel inlet system 105 being off for the middle three seconds of the seven-second spray sequence.

It is preferred that the snorkel inlet system 105 turn off when the spray bar nozzles 70 are at about neck level or about the upper chest level. In order to minimize inhalation or soft tissue exposure of the sprayed mist while the snorkel inlet system 105 is off, a user is typically instructed to close their eyes and hold their breath for the three seconds that the snorkel inlet system 105 is off, allowing the sprayed mist to fall on the face. As soon as the user hears the snorkel inlet system 105 turn on, the user can start breathing again. Alternatively, a signaling system could also be used, such as a pre-recorded manual countdown to give the user advance notice, such as "3-2-1, close your eyes and hold your breath for the next three seconds, 3-2-1 resume breathing".

In one embodiment of the invention, the snorkel inlet system 105 uses a 250 cubic feet/meter (CFM) and positive pressure fan unit 100 connected to the snorkel housing 107 through a four inch conduit hose element 111. However, the present invention is not restricted to these specifications, and other CFM ratings and conduit diameters will be readily apparent to one skilled in the art. Exemplary but not exhaustive examples would include positive pressure fans rated from 125-500 CFM, and conduit diameters possibly ranging from two inches to five inches. Moreover, the fan speed of the positive pressure fan unit 100 could also be adjusted to increase or decrease the rate and amount of air pushed into the facial area of the user.

Either or both of the inlet component 105 or exhaust component 120 maybe configured to operate immediately upon the entry of a user into the booth 10 as detected by the opening the door 50 or through a signaling received by a vicinity detection system (not shown). In other configurations, the subsequent entry of a user into the booth and closure of the door 50 may cause the inlet component 105 and/or exhaust component 120 to turn on. The user may also manually adjust the snorkel nozzle 106 and/or the positive pressure fan 100 speed for a preferred pressure provision at the user's facial area.

Although the present embodiment has only one moving spray bar 72 of spray nozzles 70, alternative embodiments may have additional spray bars (not shown) of spray nozzles 70, so that two or more sides of a person are being sprayed simultaneously. Where only one moving spray bar 72 is provided, as in the present embodiment, it is preferred that the user initiate a spraying sequence for one side of the body, then reposition by turning 180 degrees from the initial position and initiating a second sequence to spray the other side of the body, with two cycles, therefore, required for one spray tanning session per person.

A cable chase 130 is provided at the rear of the spray booth 10 for housing electronic cabling and supporting the drive motor 82 that operates the drive chain 81 to convey the spray 74 up-and-down by the rolling of the convex rollers 76 along the outer surface 53 of the support poles 54. In one embodiment, the cable chase 130 is a four inch by four inch aluminum housing, wherein the cable chase 130 and other aluminum support structures 132 are fabricated from half-inch aluminum. However, other appropriate materials and thicknesses for fabrication will be readily apparent to one skilled in the art, and the present invention is not restricted to the embodiments described herein.

A further improvement of the invention may be found in alternative embodiments wherein the downdraft system vents 122 are located behind and distal to the user relative to the location of the positive pressure snorkel inlet system 105. This arrangement both pushes mist across the body and pulls it down on the opposite side of the body positioned before the spray nozzles 70 and, therefore, provides an improved rate of removal of the atomized mist from the spray nozzle 70 regions. This is an additional improvement over prior art venting systems that draw across the jet area and, therefore, across a user's face when facing the jets. Thus, the ventilation system may be configured to provide a push-pull type of system. The directional snorkel then pushes air in front of a user's face while the downdraft exhaust system pulls mist away from facial areas.

Alternative embodiments of the positive pressure inlet snorkel nozzle 106 may also be provided. For example, a long snorkel-type inlet may send from the ceiling/top cap 30. The originating location of the inlet snorkel 106 is not important; what is important is that it is adjustable—manually or automatically—to provide a fresh air input into the facial area of the user.

Accelerated Drying of Topical Skin Treatments

Figure 8:
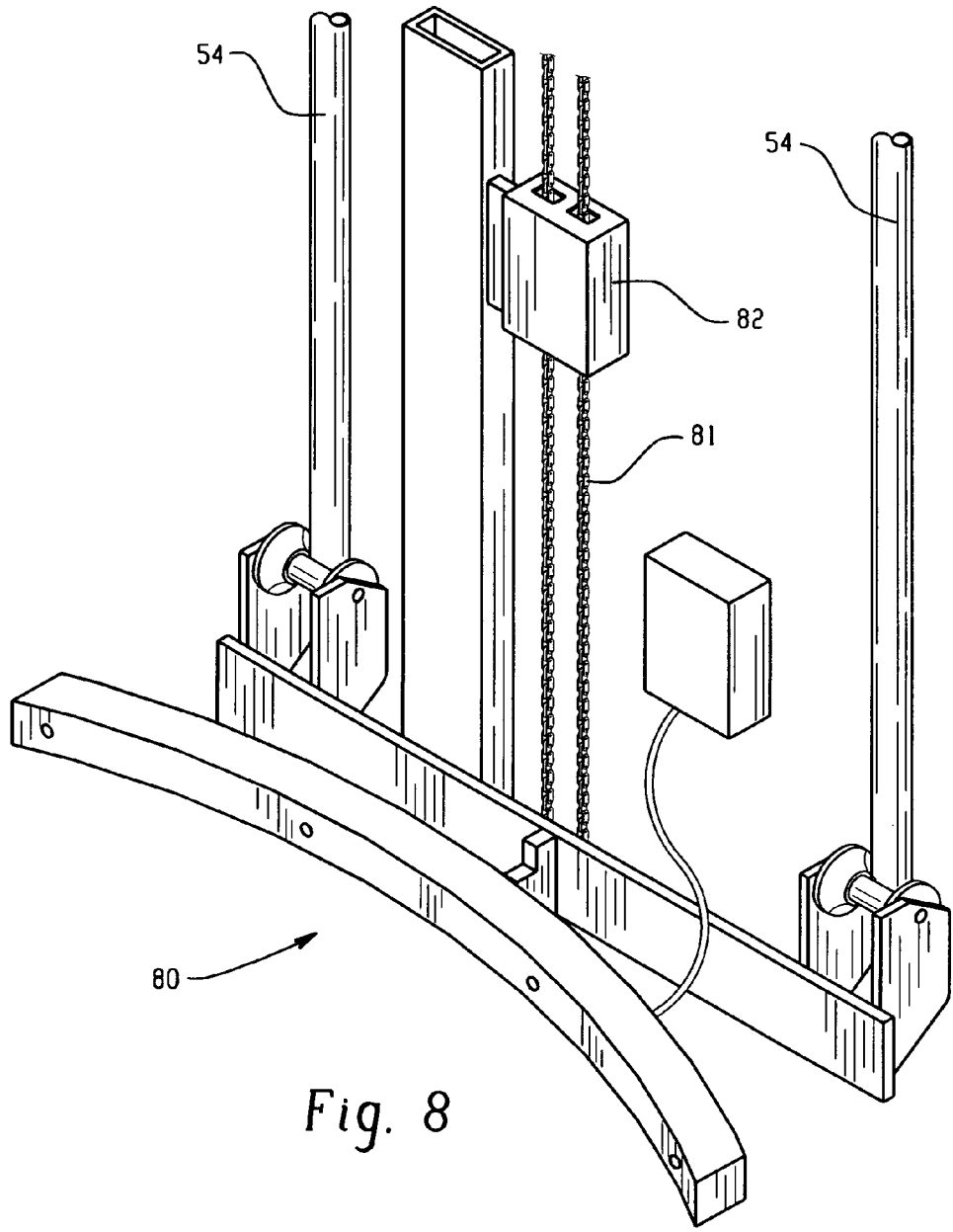
Figure 9:
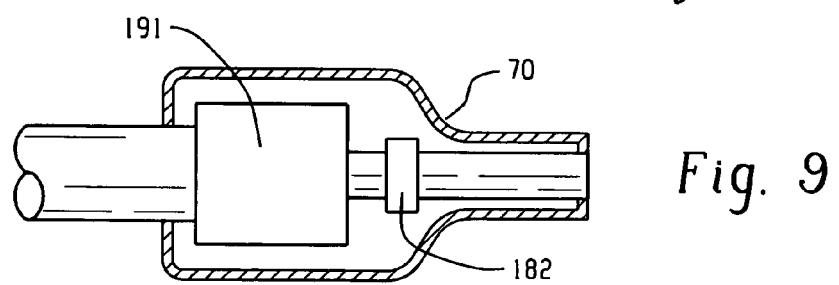
Figure 10:
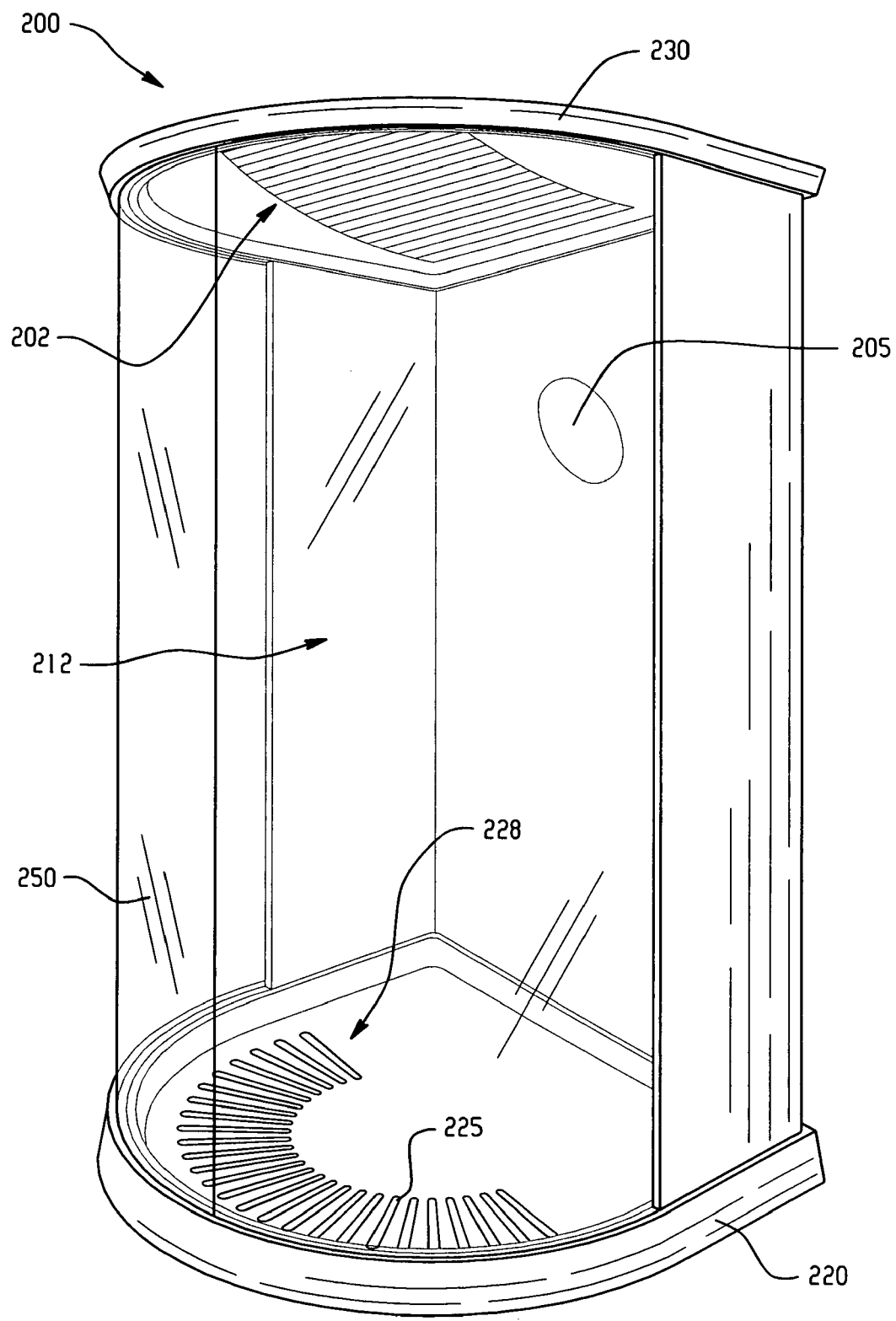
Figure 11:
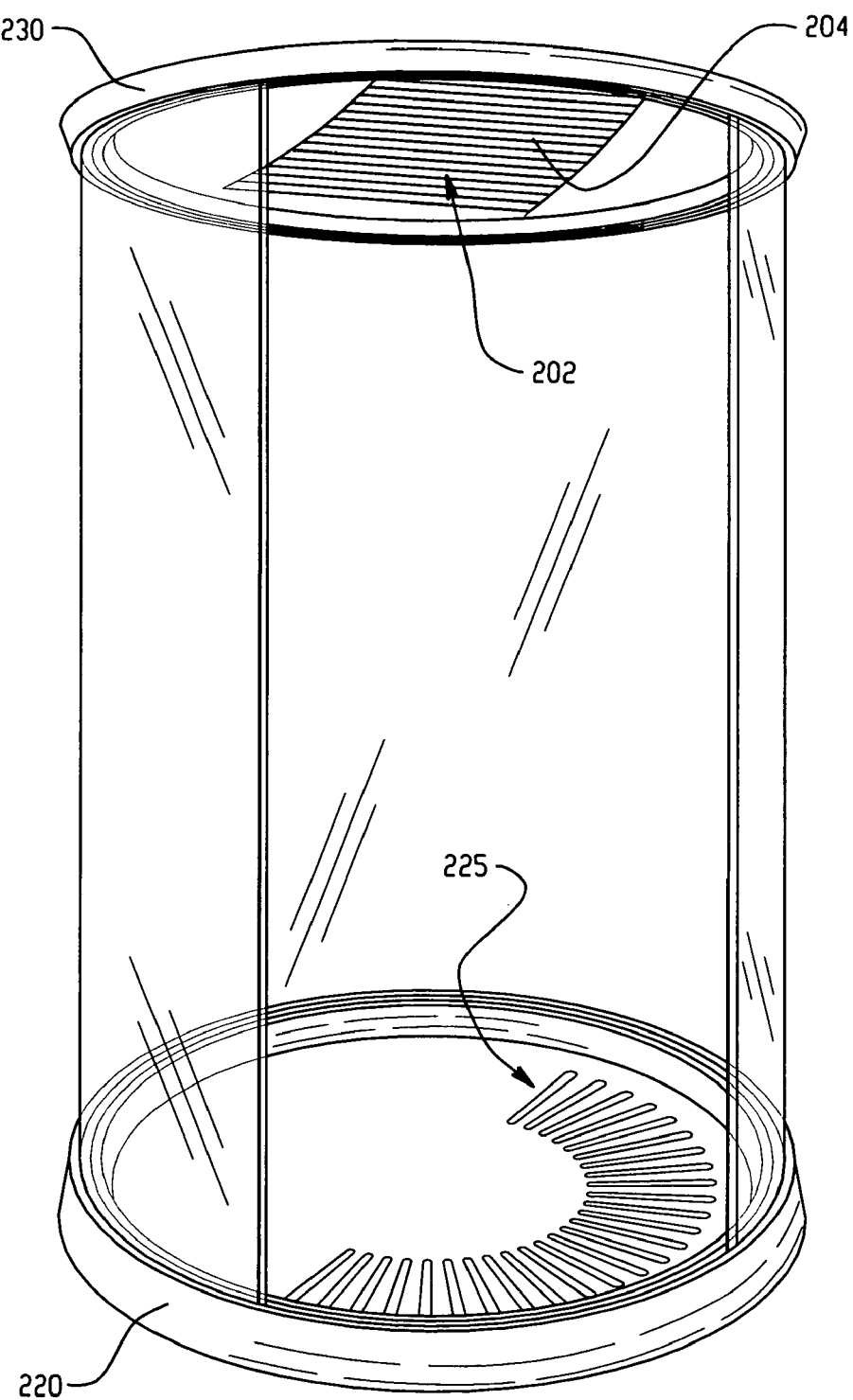
Figure 12:
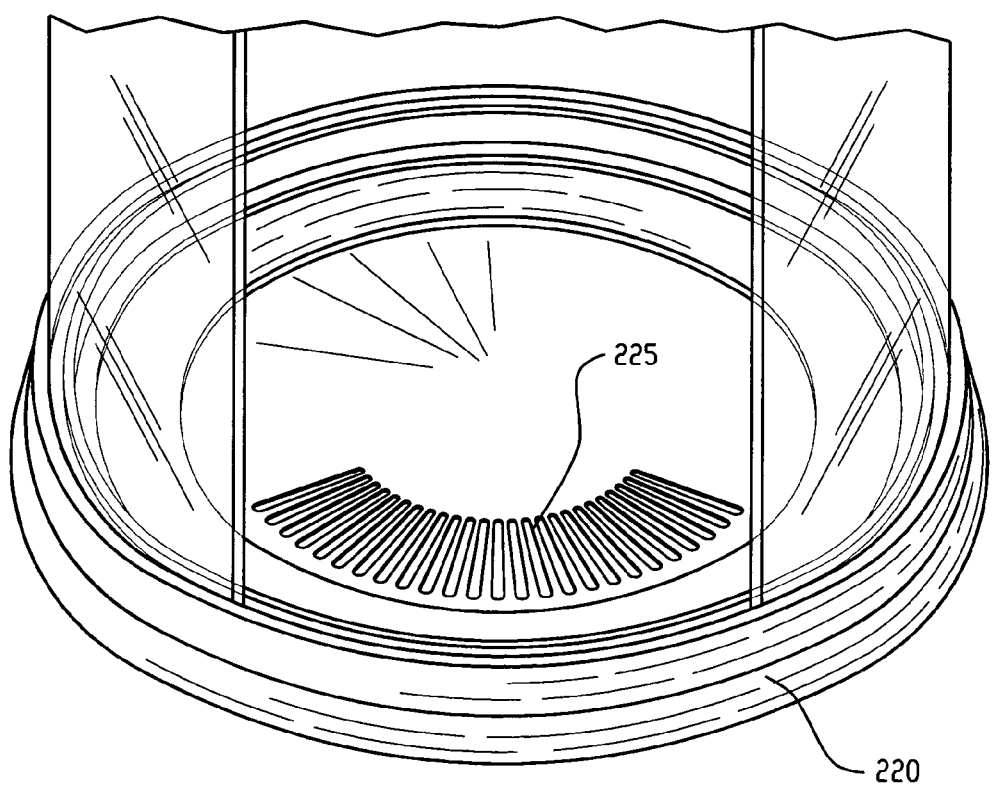

Some embodiments of the present invention also provide a novel "touch-less skin drying" feature. Referring to another embodiment 200 of the present invention in FIGS. 8-10, a large blow dryer 202 is provided in the top cap 230. After a spray session is completed the blow dryer 202 is turned and a large quantity of air is blown forcefully down from the top of the entire booth enclosure 212 in a rapid fashion. In one embodiment, a big "WHOOSH" of air will come down and rapidly blow dry the user, thereby obviating the need for the user to towel-dry excess atomized mist (and, thus, tanning solution) off of the skin in order to dry the skin to a level of comfort and to dress with clothing without staining and/or wetting the clothing with atomized solution still wet upon the skin.

Since more of the tanning compounds will thus be left upon the skin than where a user wipes off excess with a towel, the present invention will improve the extent and quality of the resultant tan. It will also further provide a more uniform tanning result, since it prevents the uneven tanning compound application that results when towel drying removes more tanning compounds from some areas of the skin than from others.

As it is common for users to desire a generally warm and pleasing experience, the blown air may be heated by being compelled through heated elements, such as electrical resistors. In other embodiments, heat can be provided through infrared heat lamps, such as those commonly found in consumer bathroom lighting and ventilation units, and the air itself is not heated. In some embodiments, heating elements may be turned off or on by a user, salon operator or automatically, and, therefore, in the summertime or within the other warm environments, the heating of the blown air maybe be de-selected. Furthermore, the air itself may be cooled instead of heated, as through air-conditioning units, where a cool or cold experience is, in fact, desired and selected.

Where the exhaust system snorkel 105 and downdraft exhaust 120 remain activated, this "touch-less skin drying" feature will also increase air flow across the user's face and body to thereby further assist in removal of the ambient atomized mist and further reduce soft tissue and inhalation exposures, and also give more positive pressure to more rapidly exhaust ambient atomized mist through the exhaust vents.

In the second invention embodiment 200 a sliding track door 250 is provided. In some configurations, once the door 250 is opened, the large blow dryer 202, the particular positive pressure snorkel input system 205 and downdraft exhaust system 228 automatically shut off. Alternatively, the embodiment 200 may be programmed to leave one or more of the blow dryer 202, input system 205 and downdraft exhaust system 228 on for a given time period after the door 250 is opened and/or the absence of a user from the booth is detected by some type of vicinity detection system (not shown), or a manual switch may be provided for one or more of the blow dryer 202, input system 205 and downdraft exhaust system 22.

Solution Reservoir Sensor Circuitry

Another novel and advantageous characteristic of the current invention is the provision of sensor circuitry 172 within the atomizing solution reservoir 170. The sensor circuitry 172 tacitly monitors the amount of atomizing solution present in the reservoir 170. In some embodiments of the invention, once a predetermined low-level of solution is detected, automatic notification is provided. Automatic notification may be utilized locally, to notify a user or salon owner to manually refill the reservoir. Alternatively, it may also be used for automatic notification of a remote distributor. For example, the sensor circuitry 172 may be configured to interface with an e-mail server component 173 of a computer system 174. Responsive to a predetermined low-level setting, the e-mail server 173 may automatically send an e-mail notification to a prearranged distribution service ("Come fill me—we're getting low!"), and replacement atomizing solution will be responsively ordered and sent from the distribution center to the booth location. The actual arrival of the replacement shipment may thus function as notification to a salon operator that his solution is low.

In another embodiment of the invention, a spray booth control system may keep count of every spray sequence initiated and/or completed. By tracking every single use, distribution of additional replacement atomizing solution may be triggered by reaching a threshold number of spray sessions since the last shipment. Monitoring of the number of spray sessions and/or the use of atomizing solution may also be useful in calculating the lease or amortization payments, or licensing obligations, dependent upon equipment or materials use, or user account activity.

Variable Pulse Solenoid Spray Nozzles

Another advantage of the present invention is the use of variable pulse focus spray technology solenoid nozzles for the nozzles 70 in some embodiments. These are much higher pressure than the conventional air atomizing nozzles used in prior art spray booths. Each of the variable pulse nozzles has a built-in solenoid 181, which turns on and off at a high frequency, to generate a corresponding high frequency pulsing. The pulsing provides advantages over air atomizing nozzles breaking up the solution into mist and compelling under pressure in a focused dispersion without requiring a separate air pressure component. Therefore, no air compressor or other high-pressure air system component is required to atomize the solution and compel the atomized solution toward the user. All that is required is a pump means 180 to provide high fluid pressure for and through the pulsing solenoid 181. Both of the atomizing and mist compelling functions are accomplished by the rapidly pulsing wave form behavior of the solenoid 181. High pressure coming in goes through the vibrating solenoid 181 element which helps spread it out rather than responsively spraying the liquid in a narrow focused stream. Without the vibrating solenoid element 181, then the nozzle 70 would just spray the liquid like a high pressure jet right at the user. What causes the fluid to break up and convey outwardly in a mist is the pulsing solenoid.

Exemplary pulse frequencies include those within the 4000-6000 cycles per minute range; however, pulse rates as high as 10,000 cycles per minute are practical with the present solenoid pulse nozzles 70.

Fluid Pressure Feedback Control System

Prior art fluid pressure input to the air atomizing nozzles should remain within a preferred pressure range in order to generate a constant nozzle output pressure. Prior art spray booths, therefore, typically use a regulator to manually adjust a preferred maximum fluid delivery pressure for a mixture of air with the fluid. Fluid pressure, i.e. anything in excess of the maximum pressure, has to bypass the atomizing nozzles and return the excessively pressurized liquid back to the original tank. What is new in the present invention is a feedback control system 190 in communication with the variable pulse solenoid nozzles 70. By providing for an automatic feedback system 190, the operation of the spring nozzles 70 can be factory set in a closed control system. There is no need for any end-user adjustments to keep and maintain a desired nozzle output pressure. A pressure detection circuitry element 191 within the solenoid nozzle 70 measures the pressure of the atomized liquid being projected by the nozzle 70 and provides feedback to the control system 190 to adjust the output pressure accordingly. This aspect of the invention provides advantages in cost efficiency, increased reliability, less on-time site requirements for technician time to adjust the spray booth nozzle outputs, and more uniformity of spray delivery precision from the booth. An operator can more accurately predict how much liquid atomizing solution will actually be over a given number of spraying sessions, as well as over the operating lifetime of the machine, providing more efficient use of resources and superior quality control. The end-user will receive a predictable and reliable "tan" over the same acceptable parameters for every use.

In one embodiment wherein the nozzles 70 are air atomization nozzles, the feedback system 190 is configured to maintain a nozzle 70 output pressure of 40 pounds per square inch (psi), although other embodiments may provide for greater or lesser pressures. In some fluid pressure-only nozzle 70 embodiments, the feedback system may be set to maintain a target output pressure within a 120-250 psi range, although other pressures and ranges are possible.

Temperature Controlled Topical Skin Treatments

In other aspects of the invention, the mist fluid may itself be heated or cooled prior to atomization. For example, the fluid may pass through an in-line temperature modifying system 195 prior to being pumped to and through the nozzles 70, thus improving the comfort of the tactile experience of the user in receiving the atomized mixture upon the skin.

The temperature modifying system 195 may be configured to heat or cool the fluid. It may also be configured to perform either of the heat or cool functions as manually or automatically selected or required responsive to system parameters. Therefore, the temperature modifying system 195 may thus "heat the mist" by preheating the fluid prior to its arrival at the atomizing nozzles 70. This will provide a more pleasurable experience for the user, as many prior art spray booth users complain that they do not like the experience of being sprayed with a "COLD" spray mist. Alternatively, the temperature modifying system 195 may cool the liquid and, thus, the atomized mist, which may be desired in hot weather climates and/or seasons or in hot environments where the comfort level of a user would be improved by a cooling atomized mist experience.

Where the nozzles 70 are configured to utilize compressed air in projecting the atomized mist, the air entraining the atomized mist produced by the nozzles 70 may be instead heated or cooled, such as, for example, through radiant heat emitting infrared lighting, electrical resistor circuitry, or air conditioning systems. In some embodiments of the invention, either or both of the air and the liquid may be pre-heated or pre-cooled. The advantages of this improvement include not only increasing the comfort level of the user, but in effecting a better quality tan by relaxing and opening the pores of the skin of a user receiving an atomized tanning solution mist.

The embodiments of the inventions described above may be tangibly embodied in a computer program residing on a computer-readable medium or carrier. The medium may comprise one or more of a fixed and/or removable data storage device such as a floppy disk or a CD-ROM, or it may consist of some other type of data storage or data communications device. The computer program may be loaded into a memory unit to configure a processor unit within an apparatus power and/or control system for execution, or within another system and associated controller, remote or local. The computer program comprises instructions which, when read and executed by a processor unit, causes the processor unit to perform the steps necessary to execute the steps or elements of the present invention.

While preferred embodiments of the invention have been described herein, variations in the design may be made, and such variations may be apparent to those skilled in the art of sunless spray tanning booths and systems, as well as to those skilled in other arts. The materials identified above are by no means the only materials suitable for the manufacture of the present invention, and substitute materials will be readily apparent to one skilled in the art. The scope of the invention, therefore, is only to be limited by the following claims.

I claim:

1. A downdraft exhaust apparatus for removing an atomized liquid solution from an enclosure, comprising:
    an enclosure booth defined by at least one vertically oriented enclosure wall and a vertically oriented door, the at least one wall and the door disposed between and connected to a horizontally oriented bottom tray and a horizontally oriented top cap;
    an exhaust vent located below an anticipated user's facial area zone, the exhaust vent disposed within the bottom tray or a lower area of the at least one wall or a lower area of the door, the vent configured for exhausting ambient atomized liquid solution from the spray enclosure booth; and
    an exhaust system pneumatically connected to the exhaust vent, whereby the exhaust system is configured to exhaust ambient atomized liquid solution from the enclosure booth by drawing said atomized solution into the exhaust vent downward relative to the anticipated user's facial area zone, and then out of the enclosure; wherein the exhaust system is comprised in at least one hollow, cylindrical support pole that is attached to the bottom tray and supports the top cap, the air is drawn through the vent to travel in the support pole to a negative pressure exhaust fan pneumatically connected to the exhaust system at a top of the top cap.

2. The downdraft exhaust apparatus of claim 1, further comprising a positive pressure fresh air inlet vent configured to direct fresh air into the enclosure in the anticipated user's facial area zone, the positive pressure air inlet unit is attached to an adjustable nozzle so that the air blown into the apparatus can be redirected.

3. The apparatus of claim 1, further comprising a positive pressure fan dryer located in the enclosure top cap and configured to forcefully blow air down onto the skin surface of the person after the skin surface has received the atomized liquid solution from the atomized liquid solution from the atomizing spray head and dry the skin surface; and, a heating element placed in front of the positive pressure fan to heat the air compelled from it.

4. The apparatus of claim 1 further comprising:
    an atomizing spray head assembly having at least one curved atomizing spray head, said spray head assembly movably connected to the rigid conduit support and physically supported by said rigid conduit support; and,
    solenoid pulse nozzles that generate a high frequency pulsing corresponding to a high frequency that is turned on and off by means of a built in solenoid.

5. The apparatus of claim 4, wherein a feedback control system is in communication with the variable pulse solenoid nozzles.

* * * * *